(12) United States Patent
Farr et al.

(10) Patent No.: US 6,572,609 B1
(45) Date of Patent: Jun. 3, 2003

(54) PHOTOTHERAPEUTIC WAVEGUIDE APPARATUS

(75) Inventors: Norman E. Farr, Monument Beach, MA (US); William E. Wieler, Pocasset, MA (US); Lincoln S. Baxter, Centerville, MA (US); Jon T. McIntyre, Newton, MA (US); Edward L. Sinofsky, Dennis, MA (US)

(73) Assignee: CardioFocus, Inc., Norton, MA (US)

( * ) Notice: Subject to any disclaimer, the term of this patent is extended or adjusted under 35 U.S.C. 154(b) by 160 days.

(21) Appl. No.: 09/602,420

(22) Filed: Jun. 23, 2000

Related U.S. Application Data

(63) Continuation-in-part of application No. 09/357,355, filed on Jul. 14, 1999.

(51) Int. Cl.⁷ .............................................. A61B 18/20
(52) U.S. Cl. ............................ 606/15; 606/10; 606/17; 607/89; 128/898
(58) Field of Search .................. 607/88–96; 606/10–17, 606/40–47; 28/898

(56) References Cited

U.S. PATENT DOCUMENTS

| | | |
|---|---|---|
| 4,625,724 A | 12/1986 | Suzuki et al. |
| 4,701,166 A | 10/1987 | Groshong et al. |
| 4,718,417 A | 1/1988 | Kittrell et al. |
| 4,878,725 A | 11/1989 | Hessel et al. |
| 5,071,417 A | 12/1991 | Sinofsky |
| 5,078,681 A | 1/1992 | Kawashima |
| 5,125,925 A | 6/1992 | Lundahl |
| 5,242,438 A | 9/1993 | Saadatmanesh et al. |
| 5,261,904 A | 11/1993 | Baker et al. |
| 5,350,375 A | 9/1994 | Deckelbaum et al. |
| 5,368,564 A | 11/1994 | Savage |
| 5,464,404 A | 11/1995 | Abela et al. |
| 5,507,725 A | 4/1996 | Savage et al. |
| 5,800,482 A | 9/1998 | Pomeranz et al. |
| 5,830,209 A | 11/1998 | Savage et al. |
| 5,833,682 A | 11/1998 | Amplatz et al. |
| 6,012,457 A * | 1/2000 | Lesh .......................... 128/898 |
| 6,120,496 A * | 9/2000 | Whayne et al. ............... 606/41 |

FOREIGN PATENT DOCUMENTS

| | | |
|---|---|---|
| EP | 0299448 | 7/1988 |
| EP | 0311458 | 10/1988 |
| WO | 9737714 | 10/1997 |

* cited by examiner

Primary Examiner—David M. Shay
(74) Attorney, Agent, or Firm—Thomas J. Engellenner; Tram Anh T. Nguyen; Nutter McClennen & Fish LLP

(57) ABSTRACT

Methods and apparatus are disclosed for forming annular lesions in tissue. The methods include introduction of an optical apparatus proximate to a tissue site, via, for example, a catheter. The optical apparatus includes a pattern-forming optical waveguide in communication with a light transmitting optical fiber. Energy is transmitted through the optical fiber, such that radiation is propagated through the optical fiber and the waveguide projects an annular light pattern, e.g., a circle or a halo.

29 Claims, 4 Drawing Sheets

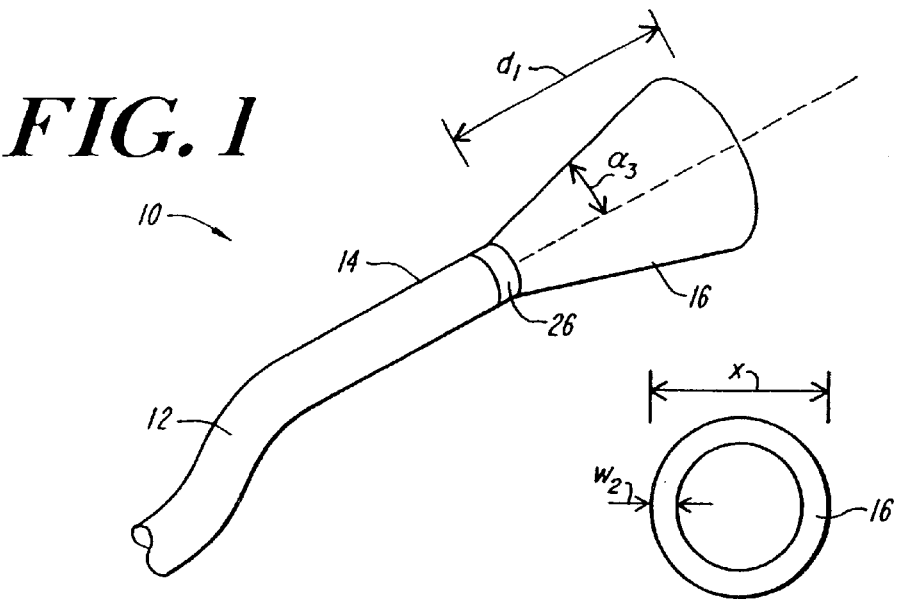
FIG. 1
FIG. 1A
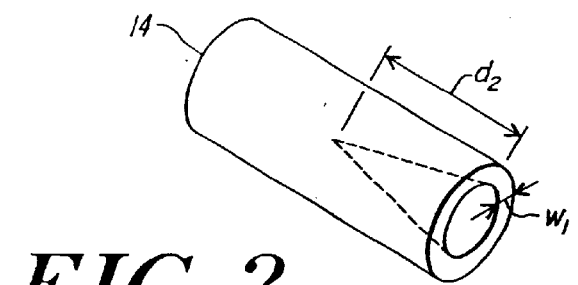
FIG. 2
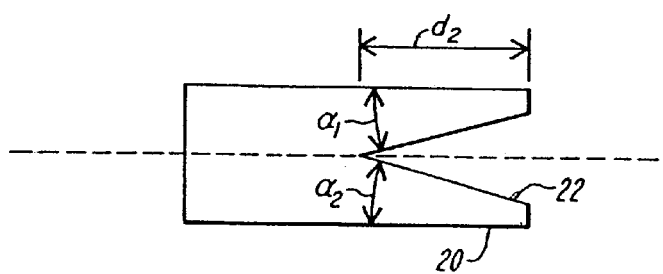
FIG. 3

PHOTOTHERAPEUTIC WAVEGUIDE APPARATUS

CROSS-REFERENCE TO RELATED APPLICATIONS

This application is a continuation-in-part of and claims priority to U.S. patent application Ser. No. 09/357,355 filed on Jul. 14, 1999, the contents of which are incorporated herein by reference.

BACKGROUND OF THE INVENTION

The technical field of this invention is phototherapy and, in particular, methods and devices which employ optical fibers and flexible light waveguides to deliver radiation to a targeted site, such as the heart.

Cardiac rhythm irregularity, i.e., fibrillation, is a pathological condition of heart muscle that can be present in one or more of the atria or the ventricles of the plant. Until recently, efforts to alleviate these irregularities have focused on pharmacological treatments. While pharmacological treatments can be effective, drug therapy requires regular administration of so-called "beta-blocker" type drugs or prompt intervention with a therapeutic inhibitor of fibrillation. Moreover, drug therapy is frequently accompanied by side effects such as dizziness, nausea, vision problems or other difficulties.

Abnormal arrhythmias can occur in the atrium or ventricle, and are referred to, respectively, as at rial fibrillation and ventricular fibrillation. Atrial fibrillation is an atrial arrhythmia characterized by rapid randomized contractions of the atrial myocardium, causing an irregular, often rapid heart rate. Three of the most common types of atrial arrhythmia are ectopic atrial tachycardia, atrial fibrillation and atrial flutter. Atrial fibrillation can result in significant patient discomfort and even death due to an irregular heart rate. Ventricular fibrillation is an arrhythmia characterized by fibrillary contractions of the ventricular muscle due to rapid repetitive excitation of the myocardial fibers without coordinated contraction of the ventricles. Loss of synchronous atrioventricular contractions compromises cardiac hemodynamics and can lead to varying levels of congestive heart failure, or stasis of blood flow, which increases the likelihood of thromboembolism. It is difficult to isolate a specific pathological cause for atrial fibrillation although it is believed that the principle mechanism is one or more of the electrical reentry circuits within the left and/or right atrium. Such reentry circuits interfere with the normal rhythm of electrical signals that course the heart muscle to contact in a synchronized manner in order to perform its normal pumping function.

Recently, it has been suggested that arrhythmias can be treated by ablation procedures performed within the heart and/or the coronary blood vessels. Ablation of predetermined locations within the heart to form linear tracks or scars through the walls (transmural) of the heart or blood vessels can provide a natural barrier to the formation of reentry circuits. These linear scars must be well defined within the heart to be effective. For example, the ablation catheters used to perform the ablation procedures produce scar tissue at the selected site from one of a number of different energy sources employing direct current, laser, microwave, or ultrasound energy. However, many of these energy sources are limited by the requirement that physical contact with the tissue to be treated must be maintained during the procedure. Moreover, the present ablation systems do not provide a suitable way to know when sufficient energy has been applied to the tissue, without unnecessary scarring of exposed tissue, or to what extent the energy has penetrated the tissue.

Another serious complication of presently known ablation techniques can occur when such procedures are performed within a vein or artery. Veins and arterial blood vessels are delicate physiological structures. Traumatic stressing of a vein or artery, such as by surgery, or thermal destruction of tissue, can lead to stenosis, a reduction or collapse of the inner diameter of the blood vessel causing a reduction in blood flow. For example, many of the current techniques used to treat fibrillation are directed to ablation of tissue within the pulmonary vein, thus leading to stenosis of the site treated. Unfortunately, the resultant stenosed vessels reduces the blood flow back to the heart, thereby causing discomfort, pulmonary hypertension and other serious side effects. Often times, the patient must undergo additional procedures to treat the stenosis, which in turn causes a new site to be traumatically stressed and ultimately stenosed. This repetitive cycle can have serious consequences for the patient.

A need therefore exists which circumvents the above-described deficiencies of currently available ablation techniques for the treatment of cardiac fibrillation.

SUMMARY OF THE INVENTION

Methods and apparatus for phototherapy are disclosed in which laser light or other radiation is projected in an annular pattern without requiring direct contact of the energy source, e.g. a laser (via fiber), with the targeted tissue. The invention is particularly useful in cardiac therapy in creating annular conduction blocks in atrial chamber issue, e.g. centered about but at a defined distance from a pulmonary vein orifice or coronary sinus orifice, to eliminate aberrant wave conduction.

The invention is particularly useful for inducing phototherapeutic processes in tissue, including ablation and/or coagulation of the tissue. Typically the optical apparatus is contained within a catheter including a flexible elongate member having a proximal end, a distal end and at least one longitudinal lumen extending therebetween. The distal end of the flexible elongate member can be open or includes a transparent cap, a centering balloon, or a centering coil. The optical apparatus of the invention can be fixed or a distal location or preferably disposed within the first lumen in a manner that permits axial motion within the lumen. The optical apparatus serves to project light through, or from, the distal end of the flexible member. The optical apparatus can include an optical fiber and other light projecting elements.

The optical apparatus of the invention can include an optical fiber and a beam-shaping waveguide for projecting an annular pattern of light. Radiation, e.g., infrared, visible or ultraviolet light is propagated through the optical fiber that is optically coupled to a lens or other optical waveguide. The lens is configured to project an annular light pattern such that an annular lesion is formed in tissue. In one embodiment, the annular light pattern expands over distance like a hollow cone to project a beam in the form of a ring or a halo. The waveguide can include a graded intensity lens (GRIN) or other known refractive or reflective optics to project the annular light pattern.

The apparatus of the invention can also include a balloon member fixedly attached to the catheter. Injection of a solution or gas expands the balloon, thereby forcing blood and/or other body fluids from the tissue site.

In certain embodiments, the optical apparatus of the invention is slidably positioned within the lumen of a catheter proximate to a tissue site. Positioning the optical apparatus at the particular location within the balloon and/or by adjusting the size or shape of the balloon permits control over the size and distance of the forwardly projected annular ring. This control permits the annular beam of projected light to be dynamically changed to specifically target the atrial tissue surrounding the pulmonary veins or coronary sinus.

The present invention also pertains to methods for forming an annular lesion in a tissue by phototherapeutic processes in tissue, including ablation and/or coagulation of the tissue. The methods include introduction of an optical apparatus proximate to a tissue site via, for example, a catheter. The optical apparatus includes a pattern-forming optical waveguide that is in communication with a light transmitting optical fiber. Energy is transmitted through the optical fiber, such that radiation propagated through the optical fiber and waveguide projects an annular light pattern, e.g., a circle or a halo. By these methods, an annular lesion can be formed in a targeted tissue. In certain embodiments, the tissue forms a lumen, e.g., vascular, atrial, ventricular, arterial, venous, brachial, or urethral lumen. Preferably the methods include projecting an annular light pattern via an optical apparatus that is located at a defined distance from the target tissue.

The present invention further pertains to methods for forming annular lesions in cardiac tissue, e.g., trabecular tissue, by phototherapeutic processes that can include ablation and/or coagulation of the tissue. The methods include positioning an optical apparatus at a location proximate to the cardiac tissue via, for example, a catheter. The optical apparatus includes a pattern-forming optical waveguide optically coupled to a light transmitting optical fiber. Energy is transmitted through the optical fiber, such that radiation is propagated through the optical fiber, the waveguide and GRIN lens to forwardly project an annular light pattern, e.g., a circle or a halo. In a preferred embodiment, a balloon is inflated against the tissue, thereby forcing blood and/or body fluids away from the tissue targeted for treatment. Light energy is then passed through the optical apparatus onto the targeted tissue such that an annular beam is projected onto the site, thereby causing ablation, coagulation or photochemical processes to occur.

The present invention also pertains to methods for treating or preventing atrial arrhythmias by phototherapeutic processes in atrial tissue. These processes can include ablation and/or coagulation of the tissue. The methods include introducing an optical apparatus proximate to atrial tissue via, for example, a catheter. The optical apparatus includes an optical waveguide in communication with a light transmitting optical fiber. Energy is transmitted through the optical fiber, such that radiation is propagated through the optical fiber and the waveguide projects an annular light pattern. The annular light pattern forms an annular lesion in the atrial tissue, thereby treating or preventing atrial arrhythmias.

In another aspect, the present invention is directed to methods of treating atrial arrhythmia. The methods include introducing a photoablation instrument into an atrium, positioning the photoablation instrument at a location within the atrium where light from an optical assembly can be projected onto an inner surface of the atrium, and exposing a region of atrial tissue surrounding a pulmonary vein to radiation from an optical assembly without substantial ablation of the vein itself. The photoablation instrument includes an optical assembly for projecting a beam of radiation, e.g., an annular beam of radiation. The optical assembly can include an optical fiber and a GRIN lens and/or other refractive or reflective elements.

In certain embodiments, the resultant annular lesion has a mean diameter of between about 10 mm and 23 mm, preferably, greater than 10 mm, more preferably greater than 15 mm, and in some instances preferably greater than 20 mm or even greater than about 23 mm. Generally, the annular lesion has a width (of the annular ring) of less than 5 mm, preferably about 3 mm, and in some applications preferably less than or equal to 1.5 mm. Preferably, the treatment occurs without ablation of into the pulmonary vein tissue. For example, the center of a pulmonary vein at its mouth in an atrial chamber can be defined with an anchorage element as described below. A annular beam of radiation can be projected to form a ring like lesion concentric with the pulmonary vein center, but at a radial distance of at least 5 mm, preferably greater than 7 mm from the vein's centerline.

According to another aspect of invention, a region of atrial tissue surrounding the targeted pulmonary vein is exposed to infrared radiation from the optical assembly at a wavelength ranging from about 805 nm to about 1060 nm, more preferably from about 900 nm to about 1000 nm and most preferably from about 940 nm to about 980 nm. More generally, the energy and wavelength of the radiation are chosen to penetrate substantially the entire thickness of the atrial wall, e.g., between about 1 to about 4 mm, preferably, between about 2 to about 3 mm in depth.

In one embodiment of the present invention, the photoablation instrument includes an expandable balloon element adapted to surround the optical assembly upon inflation. The balloon element can be inflated with deuterium oxide or deuterated water, such that the inflated balloon provides a low loss transmission pathway for radiation between the optical assembly and an inner surface of the atrium. A region of atrial tissue surrounding a pulmonary vein can then be exposed to radiation from the optical assembly. Deuterium oxide provides the advantage that it absorbs less energy from the transmitted energy, thereby preventing the balloon from becoming heated.

In still another aspect, the present invention provides a phototherapeutic apparatus that includes a light transmitting optical fiber, a graded index lens and a conical reflector. Radiation propagated through the optical fiber when connected to the graded index lens is partially reflected by the conical reflector, to project an annular pattern of phototherapeutic radiation. In a preferred embodiment, a high refractive index material, such as silicone, is in communication with the optical fiber and graded index lens and the graded index lens and conical reflector. Typically, the optical fiber and graded index lens are located between about 0 mm and about 2 mm of each other and the graded index lens and the conical reflector are located between about 0 mm and about 0.5 mm of each other. A preferred graded index lens has a length of 1.66 mm and a diameter of 1 mm.

The methods of the invention can be performed therapeutically or prophylactically. In one embodiment, the treatment method is performed on the atrial wall around the atrial/pulmonary vein juncture or around the pulmonary vein or coronary sinus, e.g., not inside the atrial or pulmonary vein but about the pulmonary or atrial surface. A circular or ring-like section outside the pulmonary vein is created by the method of the invention. Formation of one or more circular lesions about the outside diameter of a vein, impedes the conduction of irregular electrical waves in the atrium.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein:

FIG. 1 is a schematic perspective view of an optical apparatus of the invention which projects an annular beam of light from a modified waveguide;

FIG. 1A is an end view of an annular beam of light projected by the apparatus of FIG. 1;

FIG. 2 is a cross sectional view of a modified waveguide of the invention;

FIG. 3 is another cross sectional view of a modified waveguide of the invention;

DETAILED DESCRIPTION OF THE INVENTION

Figure 4:
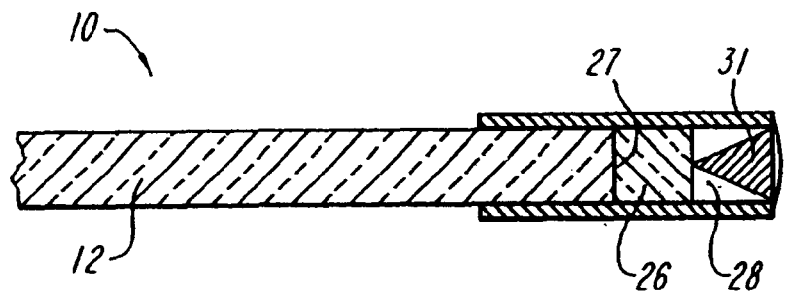
FIG. 4 is a schematic view of an optical apparatus of the invention that projects an annular beam of light from a conical reflector.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention is based, at least in part, on a discovery that the present invention can be used for inducing hyperthermia, coagulation or phototherapeutic processes in tissue, e.g., ablation, degradation, or destruction of tissue, at a specified site in tissue without harming the surrounding tissue. The results are surprising and unexpected since the efficiency and efficacy of coherent light is generally diminished by light scatter, formation of "hot spots" due to inefficient light scatter, by the limitation that the light emitted from an optical fiber continues in a straight path, and/or from interaction(s) with blood and/or body fluids which surround a tissue site to be treated.

Prior to this invention, the energy emitter, e.g., a laser source, ultraviolet light, microwave radiation, radiofrequency, etc., has generally been required to be in contact with the tissue to effect a therapeutic or prophylactic treatment. In contrast to known apparatuses and methods, the present invention does not require direct contact between the energy source, e.g., a laser source, and the tissue site to be treated. Moreover, in certain embodiments the methods and apparatus of the invention circumvent the drawbacks of having blood or body fluid coagulate, degrade or be destroyed in the treatment area proximate to the targeted tissue due to interactions with the applied energy.

In one embodiment, the present invention is drawn to an apparatus for inducing phototherapeutic processes in tissue. These processes can include ablation and/or coagulation. Typically the optical apparatus is contained within a catheter including a flexible elongate member having a proximal end, a distal end and a longitudinal first lumen extending therebetween. The distal end or a portion of the distal end of the flexible elongate member is open, transparent, or includes a transparent cap. The optical apparatus of the invention can be slidably extended within the first lumen for projecting light through or from a distal end portion of the flexible member.

In one aspect, the present invention provides an optical apparatus of the invention that includes a pattern-forming optical waveguide for projecting an annular beam of light and a light transmitting optical fiber. Radiation is propagated through the optical fiber which is in communication with the waveguide. The waveguide is configured to forwardly project an annular light pattern such that an annular lesion is formed in tissue. Typically, the annular light pattern is projected at an angle between about 20 and 45 degrees from the center plane of the optical fiber. In one embodiment, the annular light pattern expands over distance and is in the form of a ring or a halo. Preferably, the optical apparatus further includes a graded intensity lens (GRIN) adjacent to the optical waveguide for imaging the light pattern.

The present invention provides the advantage that the annular light pattern is forwardly projected. The invention further provides that the angle of projection can be adjusted by a combination of either a GRIN lens, a waveguide, a conical reflector, and/or by the dimensions of a balloon, described infra, located proximate to the optical apparatus. The present invention, therefore, provides a beam of energy, e.g., coherent light, which is projected forwardly onto a tissue surface. This in turn provides the advantage that the optical assembly/apparatus remains separated from the treatment site. Typically, the optical assembly is positioned from about 14 mm to about 24 mm, preferably from about 16 mm to about 22 mm, most preferably from about 20 mm to about 24 mm from the tissue site with the beam of light projected forwardly over a distance of from about 14 mm to about 24 mm, preferably from about 16 to about 22 mm, most preferably from about 20 mm to about 24 mm.

In contrast to the present invention, conventional laser ablation devices rely upon on contact with target tissue sites or the projection of a focused spot of radiation. Such prior art devices can not create an annular ring about a preselected site or vary the size and/or shape of the annulus to accommodate specific exposure constraints. In addition, the present invention can project ablative energy onto a specific site, unlike cryogenic or sonic techniques that treat a site along with tissue that surrounds the site due to energy dissipation about the treatment site.

The terms "optical assembly" or "optical apparatus" is intended to include various combinations of optical fibers, lenses, waveguides, reflectors and other optical elements.

The term "phototherapeutic" is intended to include photoablative, photochemical and photothermal processes that are therapeutic and/or prophylactic in a subject.

The terms "ablate" or "ablation" or "photothermal" are well recognized in the art and are intended to include thermal coagulation and/or removal of biological tissue. Ablation also includes the desiccation of tissue by the application of heat. For example, an ablating energy, such as those described above, would be one that would cause the tissue to reach a temperature of between about 50–90° C. Ablation increases the physiological temperature of a tissue by energetic stimulation to a temperature that degrades or eradicates tissue, thereby removing diseased tissue from a localized area. Ablation can be used as a therapeutic treatment, where diseased or otherwise unwanted tissue or cells exist, or as a preventative treatment to inhibit exigent physiological aberrations, e.g., arrhythmias e.g., fibrillations or flutters, growth of undesirable tissue or cells in a specific region of an organ or viscera. In order to obtain destruction of tissue exclusively by thermal effects, it is necessary for the energy to be able to reach a threshold of destruction referred to as the "thermal dose." This threshold is a function of temperature reached and of the duration of the application. Therefore, ablation, to some degree, is based on the rise of the local temperature of tissue.

The term "coagulation" is well recognized in the art and is intended to mean the action whereby cells and/or body fluids within a treated tissue site are caused to become necrotic, thickened and/or lacking in the ability to conduct electrical activity, thereby resulting in a coherent mass by the methods of the invention. The method and apparatus of the invention permit selective, coagulation of a targeted tissue area and not blood or other body fluids which are found external, e.g., surrounding, to the target site.

The term "body fluids" is intended to encompass those naturally occurring physiological components produced by a subject to maintain stasis. These fluids typically include physiological components such as plasma, growth factors, platelets, lymphocytes, granulocytes, etc.

The term "photochemical" is well recognized in the art and includes various energetic processes, including chemical reactions initiated by photons generated by an energy source. Typically photochemical processes are associated with laser, ultra-violet light, visible light or infrared light. Photochemical processes include the generation of radicals by photons colliding with tissue. The radical species are generated within cell tissue, often times causing oxidation of the cell contents; degradation or eradication occurs after the radical species are generated. In the method of the invention, photochemical reactions are selective for the targeted tissue area and not blood or other body fluids that are found external to the targeted treatment site.

Photochemical processes cause injury to cells and tissue either by mechanical lysis or by the generation of by-products such as free radicals, e.g., such as $HO_2·$, $OH^-·$, $HO·$ and $H_2O·$, which damage cell and/or tissue membrane. These reactive by-products can interact with the localized surrounding tissue area such that the tissue is cleansed of unwanted material. Photochemical processes can involve oxidation or radical polymerization of, for example, cell walls, extracellular matrix components, cell nuclei, etc. Such photochemical processes can be induced by infrared, visible and ultraviolet light energy.

The terms "into" and "onto" are used interchangeably and are intended to include treatment of tissue by focusing energy, e.g., ablative, coagulative, or photothermal, toward the afflicted area. In some instances the energy penetrates the tissue and in other instances the energy only superficially treats the surface of the tissue. An ordinary skilled artisan would understand what depths of penetration are required and those parameters that are dependent upon the application, tissue type, area to be treated and severity of condition. Accordingly, the amount of energy used to treat the afflicted area would be attenuated based upon the disease or condition being treated.

"Interstitial cavity," as the term is used herein, encompasses interstices in a tissue or structure of a natural body structure, spaces and gaps existing between layers of tissue or existing within organs, and can include interstices within the interior of the ureter, bladder, intestines, stomach, esophagus, trachea, lung, blood vessel or other organ or body cavity, and will be further understood to include any surgically created interstice that defines an interior cavity surrounded by tissue.

The term "waveguide" is well recognized in the art and is intended to include those devices that constrain or guide the propagation of electromagnetic radiation along a path defined by the physical construction of the guide. Although optical waveguides in the form of optical fibers are preferred, other types of waveguides can be used to transmit electromagnetic radiation. Several waveguides are of importance, including hollow-pipe waveguides and dielectric waveguides. Hollow-pipe guides are used primarily in the microwave region of the spectrum, dielectric guides primarily in the optical region. Various guide shapes are possible, including circular, triangular, rectangular, or square and combinations thereof.

The term "annular" is used to describe various circumferential or ring-like patterns including circular, elliptical, polygonal and irregular shapes. The annulus is preferably a closed figure but in certain applications an open (e.g. "C"-shaped) or discontinuous annular pattern can be useful or preferred.

In preferred embodiments, the electromagnetic radiation, e.g., coherent light, is emitted from the waveguide such that the projected energy expands over a distance. For example, annular projection of laser light from a circular waveguide forms an expanding cone. The angle of the cone of light is dependent upon the angle of reflection within the waveguide, the concavity of inner walls within the waveguide and the distance to an object to which it is projected. For example, as shown in FIG. 1, optical apparatus 10 includes an optical fiber 12 in communication with an optical waveguide 14 having a concave interior. The waveguide 14 passes an annular beam of light to a GRIN lens 26. The beam that exits from distal portion 18 of waveguide 14 will expand over a distance, $d_1$. Typically, the angle of projection from the central axis of the optical fiber 12 or waveguide 14 is between about 20 and 45 degrees.

As shown in FIG. 1, the projection of a beam of light 16 from waveguide 14 expands over distance $d_1$, thereby forming an annulus, an outline of a shape formed from light passing through a modified waveguide 14 and GRIN lens 26, having a diameter which is generally larger than the diameter of distal portion 18 of waveguide 14. The diameter of the annular beam of light 16, (X), is dependent upon the distance $d_1$ from the point of projection to point of capture by a surface, e.g., a tissue site, e.g., an interstitial cavity or lumen. Typically, the diameter of X is between about 10 mm and about 23 mm, preferably greater than 10 mm, greater than 15 mm, greater than 20 mm, and most preferably, greater than or equal to 23 mm. The width, $w_2$, of the annulus is dependent upon the width $w_1$ of distal end 18, distance $d_1$, distance $d_2$, and angles $\alpha_1$, and $\alpha_2$. Width $w_2$ is typically between about 0.5 mm to about 5 mm, preferably between about 1 mm to about 4 mm, most preferably less than or equal to 1.5 mm. Varying angles $\alpha_1$, and $\alpha_2$ and distance $d_2$ maximizes or minimizes angle $\alpha_3$ about the central axis as depicted in FIG. 1. Typically, angle $\alpha_3$ of projected annular light is between about 20 and about 45 degrees, preferably between about 16 and about 30 degrees, most preferably between about 17 and about 25 degrees.

As shown in FIGS. 1, 2 and 3, the width, $w_1$, of distal portion 18 can be minimized or maximized depending upon where the modified portion, e.g., the concave portion, within waveguide 14 terminates. Typically the width, $w_1$, as shown in FIGS. 2 and 3, will be between about 0.05 mm and about 1.0 mm, inclusive, more preferably between about 0.1 mm and about 0.5 mm, most preferably between about 0.1 mm and about 0.2 mm, inclusive. The distal portion 18, therefore, can be a rim which has substantially no appreciable width, $w_1$, e.g., a point where the exterior wall 20 of waveguide 14 and interior wall 22 intersect. Interior walls 22 of the tapered concave surface meet at position 24 within waveguide 14. In general, the diameter of waveguide 14 is between about 0.2 mm to about 1.0 mm, inclusive, more preferably between about 0.3 mm to about 0.8 mm, inclusive, and most preferably between about 0.4 mm to about 0.7 mm, inclusive.

Waveguides, as described in above and in FIGS. 1–3 can be made from materials known in the art such as quartz, fused silica or polymers such as acrylics. Suitable examples of acrylics include acrylates, polyacrylic acid (PAA) and methacrylates, polymethacrylic acid (PMA). Representative examples of polyacrylic esters include polymethylacrylate (PMA), polyethylacrylate and polypropylacrylate. Representative examples of polymethacrylic esters include polymethylmethacrylate (PMMA), polyethylmethacrylate and polypropylmethacrylate.

Internal shaping of the waveguide can be accomplished by removing a portion of material from a unitary body, e.g., a cylinder or rod. Methods known in the art can be utilized to modify waveguides to have tapered inner walls, e.g., by grinding, milling, ablating, etc. Preferably, a hollow polymeric cylinder, e.g., a tube, is heated so that the proximal end collapses and fuses together, forming an integral proximal portion which tapers to the distal end of the waveguide. In a preferred embodiment, the waveguide is flexible.

Waveguide 14 is in communication, e.g., connected, with optical fiber 12 by methods known in the art. These methods include for example, glueing, or fusing with a torch or carbon dioxide laser. In one embodiment shown in FIG. 1, waveguide 14, optical fiber 12 and, optionally, a gradient index lens (GRIN) 26 are in communication and are held in position by heat shrinking with a polymeric material 28, such as polyethylene terephthalate (PET) about the optical apparatus 10 and, optionally, GRIN lens 26.

In an alternative embodiment, as shown in FIG. 4, GRIN lens 26 is in communication, e.g., adjacent to, with optical fiber 12 by methods known in the art. These methods include for example, glueing, thermal bonding or fusion. In one embodiment shown in FIG. 4, optical fiber 12, GRIN lens 26 and conical reflector 31 are in communication and are held in position by welding with a polymeric material 28, such as TEFLON®, e.g., by melting the polymeric material about the optical apparatus 10 as described supra.

The distance between optical fiber 12 and the GRIN lens 26 can be from between about 0 mm and about 2 mm, from between about 0 mm and about 1.5 mm, and preferably, from between about 0 mm and about 1 mm. The gap between the optical fiber 12 and GRIN lens 26 can be filled with either air or, preferably, a high refractive material such as transparent silicone or transparent epoxy.

The GRIN lens 26, useful in this configuration generally has a length of between about 1 mm and about 2 mm, preferably from between about 1.5 mm and about 1.75 mm, and more preferably 1.66 mm. Typically, the diameter of the GRIN lens is about 1 mm.

The distance between the GRIN lens 26 and the conical reflector 31 can be from between about 0 mm and about 0.5 mm, between about 0 mm and about 0.25 mm, preferably, between about 0 mm and about 0.1 mm. Typically the gap formed between the GRIN lens and the conical reflector 31 is filled with air or, preferably, a high refractive index material, such as silicone or a transparent epoxy.

Typically the conical reflector 31 has an outer surface of a highly reflective material. For example, the surface can be coated with silver or gold. An additional layer, or layers of dielectric coating can be coated onto the reflective layer. Suitable dielectric layers include coatings of silica/titania mixtures. The apex portion of the conical reflector is positioned from about 0 mm to about 0.5 mm, generally from about 0 mm to about 0.25 mm, preferably from about 0 mm to about 0.1 mm from the distal end of the GRIN lens 26. Conical reflector 31 has a shape sufficient to deflect light transmitted from the GRIN lens 26 to a selected tissue site at an angle of from about 20 to about 45 degrees.

In preferred embodiments, the electromagnetic radiation, e.g., coherent light, is emitted through the optical fiber through the optional GRIN lens and onto the conical reflector such that the projected energy expands uniformly over a distance. For example, annular projection of laser light from a conical reflector forms an expanding cone. The angle of the cone of light is dependent upon the angle of conical reflector and the distance to an object to which it is projected. Typically, the angle of projection from the central axis of the optical fiber 12 is between about 20 and 45 degrees.

The terms "gradient index lens" or "graded index lens" (GRIN) are well recognized in the art and are intended to mean those lenses which have a refractive index distribution, which takes place in a parabolic manner so that the refractive index is greatest at the central axis of the rod and so that the refractive index is progressively reduced from the central axis toward the periphery of the rod. As a result, the penetrating light is caused to move inside the rod in a zigzag manner. The shape of the GRIN lens can be cylindrical, oval, round, or convex.

The term "flexible elongate member" is well recognized in the art and is intended to refer to a hollow tube having at least one lumen. In general, a flexible elongate member is often termed a "catheter", a term which is well known in the art. The flexible elongate member has proximal and distal ends with at least one longitudinal lumen extending therebetween. The distal end can be open or closed as is known in the art. In one embodiment, the distal end of the flexible elongate member is open, thereby allowing an optical apparatus of the invention to protrude beyond the elongate member, e.g., into a catheter end, e.g., into a balloon member. In another embodiment, the distal portion of the elongate member is closed, thereby preventing an optical apparatus from passing beyond the distal end of the elongate member.

Flexible elongate members, e.g., tubular catheters, can be formed from biocompatible materials known in the art such as cellulosic ethers, cellulosic esters, fluorinated polyethylene, phenolics, poly-4-methylpentene, polyacrylonitrile, polyamides, polyamideimides, polyacrylates, polymethacrylates, polybenzoxazole, polycarbonates, polycyanoarylethers, polyesters, polyestercarbonates, polyethers polyether block amides, polyetherketones, polyetherimide, polyetheretherketones, polyethersulfones, polyethylene, polypropylene, polyfluoroolefins, polyimides, polyolefins, polyoxadizoles, polyphenylene oxides, polyphenylene sulfides, polysulfones, polytetrafluoroethylene, polythioethers, polytraizoles, polyurethanes, polyvinyls, polyvinylidene fluoride, silicones, urea-formaldehyde polymers, or copolymers or physical blends thereof.

Preferably, the materials used to construct the flexible elongate member or the catheter end portion can be "transparent" materials, such as fluoropolymers. Suitable transparent materials include polyether block amides (PEBAX), polyethylene, nylon, polyurethanes and silicone containing polymers, e.g., silastic. Suitable fluoropolymers include, for example, fluorinated ethylene propylene (FEP), perfluoroalkoxy resin (PFA), polytetrafluoroethylene (PTFE), and ethylene-tetrafluoroethylene (ETFE). Typically the diameter of the flexible elongate member is between about 0.050 inches and about 0.104 inches, preferably between about 0.060 inches and about 0.078 inches. The diameter of at least one inner lumen of the flexible elongate member is between about 0.030 inches and about 0.060 inches, preferably between about 0.040 inches and about 0.050 inches. The length of the flexible elongate member varies with the intended application and in generally between about 60 cm and about 145 cm in length. For cardiac applications the flexible elongate member is between about 80 cm, and about 125 cm long, for bronchial applications the flexible elongate member is 125 cm long.

The term "catheter" as used herein is intended to encompass any hollow instrument capable of penetrating body tissue or interstitial cavities and providing a conduit for selectively injecting a solution or gas, including without limitation, venous and arterial conduits of various sizes and shapes, bronchioscopes, endoscopes, cystoscopes, culpascopes, colonscopes, trocars, laparoscopes and the like. Catheters of the present invention can be constructed with biocompatible materials known to those skilled in the art such as those listed supra, e.g., silastic, polyethylene, Teflon, polyurethanes, etc.

Typically, the optical apparatus of the invention is positioned proximate to the tissue targeted for treatment within a catheter. The catheter has been positioned proximate to the targeted tissue site and provides that the optical apparatus can be slidably positioned proximate to the tissue, thereby avoiding direct contact with the tissue and/or body fluids. In a preferred embodiment, a balloon is inflated against the tissue, thereby forcing blood and/or body fluids away from the tissue targeted for treatment. Light energy is then passed through the optical apparatus and balloon onto the targeted tissue such that an annular image is projected onto the site, which causes ablation, coagulation and/or phototherapeutic processes to occur within the tissue.

The terms "about" or "surrounding" when used in conjunction with the term "a coronary vessel opening" is intended to describe the atrial surface surrounding the blood vessel mouth or orifice inside the heart. Similarly, the term "about the pulmonary vein" is intended to encompass the atrial surface surrounding the pulmonary vein and/or its orifice. "Cardiac vessels" include without limitation, the pulmonary veins, the coronary sinus, the inferior vena cava and the superior vena cava. The exposed (ablated) areas preferably do not include any interior portion of the coronary vessels in order to minimize the risk of inadvertent stenosis.

The term "biocompatible" is well recognized in the art and as used herein, means exhibition of essentially no cytotoxicity while in contact with body fluids or tissues. "Biocompatibility" also includes essentially no interactions with recognition proteins, e.g., naturally occurring antibodies, cell proteins, cells and other components of biological systems.

The term "transparent" is well recognized in the art and is intended to include those materials which allow diffusion of energy through, for example, the flexible elongate member, the tip, cap and/or a catheter end. Preferred energy transparent materials do not significantly impede (e.g., result in losses over 20 percent of energy transmitted) the energy being transferred from a optical apparatus to the targeted tissue or cell site. Suitable transparent materials include fluoropolymers, for example, fluorinated ethylene propylene (FEP), perfluoroalkoxy resin (PFA), polytetrafluoroethylene (PTFE), and ethylenetetrafluoroethylene (ETFE).

The term "fixedly attached" is intended to include those methods known in the art to attach a catheter end portion, cap, or balloon to the distal portion of a flexible elongate member. Various means are known to those skilled in the art for fixedly attaching individual members of the present apparatus to each other. Such methods include thermal welding or glueing the two materials together to form a uniform seam which will withstand stresses placed upon the integral seam. For example, the catheter end portion or a tip is welded, e.g., thermal, photochemical, sonically, e.g., ultrasound, or glued, at the proximal most portion of the catheter end or tip to the distal end of the flexible elongate member. In another embodiment, the proximal end of the catheter end is affixed to the distal end of the elongate member which is itself a sealed, e.g., having a tip or a cap.

The terms "tip" or "cap" are well recognized in the art and are intended to include those devices which are used to seal the end of a luminal body. In one embodiment, the cap is non-metallic. In certain embodiments, the cap is non-porous. In a preferred embodiment, the cap is non-metallic and non-porous, e.g., a polymeric material.

The term "catheter end portion" is intended to include a separate attachable, and in certain embodiments, detachable, catheter-like portion which is located proximate to the distal end of a catheter. The catheter end portion can be fixedly attached or integrally locked into place on the distal end of a catheter by methods known in the art, e.g., glueing, melting, ultrasonic welding, "snap on" fittings, male-female fittings, etc. Preferably the catheter end portion is energy transparent. An example of a catheter end portion is a silicone balloon anchor.

The term "control handle" is well recognized in the art and is intended to include various means to manipulate the apparatus of the invention, including at least the flexible elongate member, guidewires if present, and the optical apparatus. Various control handles useful with the present invention are commercially available, such as those manufactured by Cordis Webster, Inc., 4750 Littlejohn St., Baldwin Park, Calif., 91706. When used, the control handle applies tension, e.g., stress, to the proximate end of a guidewire, thereby causing the distal end of the guidewire to bend, distort or deform. As a consequence of this action, the flexible elongate member to which the guidewire is attached, also bends, distorts or deforms in the same plane as the guidewire.

The phrase "light transmitting optical fiber" is intended to include those fibers, glass, quartz, or polymeric, which conduct light energy in the form of ultraviolet light, infrared radiation, or coherent light, e.g., laser light.

An exemplary manufacturing process suitable for joining the waveguide or GRIN lens, for example, to a glass-clad or polymer-clad optical fiber having an outer diameter of about 50 to 1,000 micrometers can begin by stripping off a buffer from the end of the fiber, e.g., exposing about 2 or 3 millimeters of the inner fiber core and its cladding. (It is not necessary to strip the cladding away from the core.) Prior to stripping, the fiber end face preferably should be prepared and polished as is known in the art to minimize boundary or interface losses.

In one embodiment, a transparent tubular structure will form a housing and attaching means for the waveguide or GRIN lens and prepared fiber end. The fiber and waveguide or GRIN lens are positioned such that they located so that the distal end of the stripped fiber and the proximal end of the waveguide are in communication. The tubular structure can be slid over the two components, thereby fixing the respective ends to each other. Preferably, a GRIN lens is placed in communication with the distal end of the waveguide or a conical reflector is placed in communication with the distal end of the GRIN lens and contained within the tubular structure. In one preferred embodiment, the housing is a Teflon® FEP or PET tubing available, for example, from Zeus Industries (Raritan, N.J.).

Preferred energy sources include laser light, in the range between about 200 nanometers and 10.5 micrometers. In particular, wavelengths that correspond to, or are near, water absorption peaks are often preferred. Such wavelengths include those between about 805 nm and about 1060 nm, preferably between about 900 nm and 1000 nm, most preferably, between about 940 nm and 980 nm. Suitable lasers include excimer lasers, gas lasers, solid state lasers and laser diodes. A particularly preferred AlGaAs diode array, manufactured by Optopower, Tucson, Ariz., produces a wavelength of 980 nm. A preferred energy is coherent light, e.g., laser light, in the range between about 200 nm to about 2.4 micrometers, preferably between about 400 to about 3,000 nm, more preferably between about 805 and 1060 nm. Typically the optical apparatus emits between about 10 to about 25 watts of power to yield an energy fluence of ablative radiation at the heart tissue surface of about 0.5 watts/cm$^2$ to about 3 watts/cm$^2$.

In one embodiment, the optical apparatus can extend beyond the distal end of the flexible elongate member. In certain embodiments, the optical apparatus slidably extends into the space created by a balloon filled with a suitable solution or gas. Alternatively, the optical apparatus can be slidably located or fixed within a transparent flexible elongate member about which surrounds an inflated balloon. In this embodiment, the light is projected annularly through the transparent flexible elongate member, through an inflation solution, e.g., deuterium oxide, and into the inflated balloon and onto the targeted treatment site.

The light transmitting optical fiber transmits the energy from an energy source which is in communication with the optical fiber. Suitable energy sources are known in the art and produce the above-mentioned types of energy. Preferred laser sources include diode lasers. The optical fiber is positioned within lumen formed by a flexible elongate member (described supra). The optical fiber can be slidably controlled within the lumen such that positioning of the optical fiber within the flexible elongate member is readily achieved. Preferably, the optical fiber is positioned proximate to the expanded balloon member.

The balloon, e.g., a biocompatible balloon, is affixed to the catheter body member near the distal end and is in fluid communication with at least one of inflation port. Upon injection of solution, the expandable balloon inflates forming a lumen or "reservoir" between the catheter body and the outer wall of the balloon. It should be understood that the term "balloon" encompasses deformable hollow shapes which can be inflated into various configurations including balloon, circular, tear drop, etc., shapes dependent upon the requirements of the body cavity.

Figure 6:
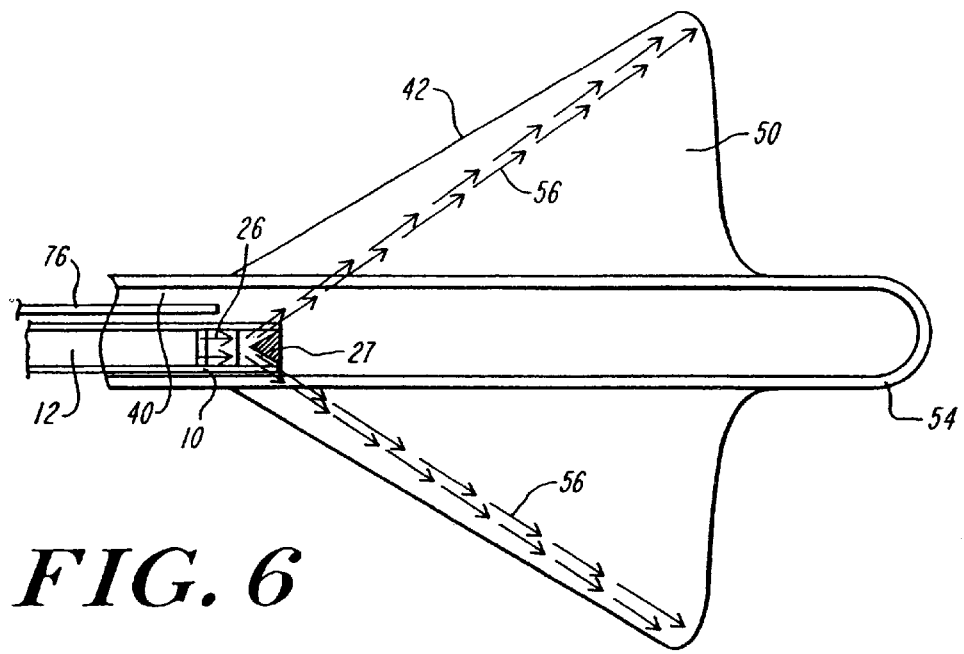
FIG. 6 is a cross-sectional view of a preferred device of the invention including an inflated balloon attached to a flexible elongate member having an optical apparatus contained therein.

In preferred embodiments useful in cardiac therapy, the balloon is configured such that the catheter does not enter into the pulmonary vein (See, for example, FIG. 6). As such, the distal region of the balloon is larger than the diameter of the pulmonary vein, thus permitting intimate contact with the atrial surface about the proximal region of the pulmonary vein. In a preferred embodiment, the balloon has a tear drop shape or a shape in which the distal end of the balloon is larger than the proximal end. The diameter of the distal portion of the balloon corresponds to the maximum diameter of the annularly projected light, thereby enabling the artisan to ablate tissue about the atrial surface in a lesion equivalent to the diameter of the distal portion of the balloon. This configuration prevents ablation of tissue within the pulmonary vein and provides the advantage of avoiding stenosis of the pulmonary vein.

The terms "treat," "treatment" or "treating" are intended to include both prophylactic and/or therapeutic applications. The methods of the invention can be used to protect a subject from damage or injury caused by a disease, physical aberration, electrical aberration, or can be used therapeutically or prophylactically treat the subject after the onset of the disease or condition.

The term "subject" is intended to include mammals susceptible to diseases, including one or more disease related symptoms. Examples of such subjects include humans, dogs, cats, pigs, cows, horses, rats and mice.

The term "tissue" is well recognized in the art and is intended to include extracorporeal materials, such as organs, e.g., mesentery, liver, kidney, heart, lung, brain, tendon, muscle etc.

The term "disease" is associated with an increase of a pathogen within a subject such that the subject often experiences physiological symptoms which include, but are not limited to, release of toxins, gastritis, inflammation, coma, water retention, weight gain or loss, ischemia and immunodeficiency. The effects often associated with such symptoms include, but are not limited to fever, nausea, diarrhea, weakness, headache and even death. Examples of diseases which can be treated by the present invention include undesirable cell proliferation, bacterial infection, cancer, e.g., bladder, urethral, mammarian, ovarian and lung cancer, or, ischemia, and benign prostatic hypertrophy or hyperplasia (BPH).

The language "undesirable cell proliferation" is intended to include abnormal growth of cells which can be detrimental to a subject's physiological well being. Effects of undesirable cell proliferation can include the release of toxins into the subject, fever, gastritis, inflammation, nausea, weakness, coma, headache, water retention, weight gain or loss, immunodeficiency, death, etc. The undesired cells which proliferate can include cells which are either benign or malignant. Examples of undesirable cell proliferation include bacterial cell proliferation and aberrant cell division and/or proliferation of foreign cells, such as in cancer cells.

The terms "aberrant cell" or "aberrant tissues" as used herein, are well recognized in the art and are intended to include aberrant cell division and/or proliferation where cells are generated in excess of what is considered typical in physiologically similar environment, such as in cancers.

The language "control of undesirable cell proliferation" or "controlling undesirable cell proliferation" is intended to include changes in growth or replication of undesired cells or eradication of undesired cells, such as bacteria, cancer, or those cells associated with abnormal physiological activity. The language includes preventing survival or inhibiting continued growth and replication of an undesired cell. In one preferred embodiment, the control of the undesired cell is such that an undesired cell is eradicated. In another preferred embodiment, the control is selective such that a particular targeted undesired cell is controlled while other cells, which are not detrimental to the mammal, are allowed to remain substantially uncontrolled or substantially unaffected, e.g., lymphocytes, red blood cells, white blood cells, platelets, growth factors, etc.

The term "cancer" is well recognized in the art and is intended to include undesirable cell proliferation and/or aberrant cell growth, e.g., proliferation.

The term "modulate" includes effect(s) targeted tissue(s) that prevent or inhibit growth of diseased tissue, which may ultimately affect the physiological well being of the subject, e.g., in the context of the therapeutic or prophylactic methods of the invention.

The term "solution" is intended to include those solutions, e.g., aqueous solutions, which can be administered to a subject through a device of the present invention without subsequent adverse effects. In particular, the solution should not diminish the strength, quality, or wavelength of energy emitted, e.g., laser energy, from the optical apparatus. In general, the solution is considered a pharmaceutically acceptable carrier or vehicle.

The term "modify" is intended to encompass those changes to the targeted tissue site, e.g., the surface, that cause the tissue to no longer have undesired properties. For example, treatment of the anterior wall of the right atrium by the present invention changes the path of electrical conduction after photonic treatment. The result is a conduction block that redirects conduction through the tissue and prevents the conduction from traveling across the atrial wall as it did prior to treatment.

The present invention also pertains to methods for forming an annular lesion in a tissue by ablation, coagulation and/or phototherapeutic processes. The methods introduce an optical apparatus proximate to a tissue site via, for example, a catheter. The optical apparatus includes a modified optical waveguide that is in communication with a light transmitting optical fiber. Energy is transmitted through the optical fiber, such that radiation propagating through the optical fiber and waveguide projects an annular light pattern, e.g., a circle, ring, halo or an outline or a shape formed by.and projected from the modified waveguide. Preferably, the light is projected through a graded intensity lens that is adjacent to the optical waveguide. This additional step attenuates aberrations in the light pattern and facilitates the forward annular projection of the therapeutic light. By these methods, an annular lesion can be formed in tissue. In certain embodiments, the tissue forms a lumen, e.g., vascular, atrial, brachial, urethral, ureteral, etc.

In another aspect, the invention includes methods for cardiac arrhythmia(s) by introducing a photoablation instrument into the heart, positioning the photoablation instrument in a location within the heart and exposing a region of heart tissue to radiation from the optical assembly. The photoablation instrument includes an optical assembly for projecting a beam of radiation as described supra and infra. One advantage of this method lies in the ability to project light from the optical assembly onto cardiac tissue within the heart in, for example, an annular pattern. Another advantage of the method is that the instrument can be positioned a distance proximate to the treatment site, thereby reducing the risk of overheating the tissue area. Consequently, this method of the invention can be used to treat, for example, the pulmonary vein, coronary sinus, inferior vena cava and superior vena cava. This method of the invention can also be useful in treating cardiac tissue associated with cardiac irregularities, e.g. arrhythmias, such as the pulmonary vein, coronary sinus, inferior vena cava and superior vena cava. Arrhythmias, for example, can occur in the atrium or ventricle, and are referred to, respectively, as atrial fibrillation and ventricular fibrillation. Atrial fibrillation is an atrial arrhythmia characterized by rapid randomized contractions of the atrial myocardium, causing an irregular, often rapid heart rate. Three of the most common types of atrial arrhythmia are ectopic atrial tachycardia, atrial fibrillation and atrial flutter. Ventricular fibrillation is an arrhythmia characterized by fibrillary contractions of the ventricular muscle due to rapid repetitive excitation of the myocardial fibers without coordinated contraction of the ventricles.

In one embodiment, the method of the invention can be utilized to treat ventricular tachycardia by projecting an annular beam onto the ventricular tissue. The annular beam focuses energy onto the tissue and forms a lesion. The lesion forms a conduction block and impedes electrical conduction through the formerly problematic tissue, thereby preventing further abnormal electrical stimulation in the afflicted cardiac tissue.

The present invention further pertains to methods for forming annular lesions in cardiac tissue, e.g., trabecular tissue, by ablation, coagulation and/or phototherapeutic processes. The methods include introduction of an optical apparatus proximate to cardiac tissue via, for example, a catheter. The optical apparatus includes an optical waveguide in communication with a light transmitting optical fiber and preferably, a GRIN lens. Energy is transmitted through the optical fiber, such that radiation propagated through the optical fiber, waveguide and GRIN lens forwardly projects an annular light pattern, e.g., a circle or a halo. By these methods, an annular lesion can be formed in cardiac tissue.

The invention can employ an optical apparatus that includes, for example, a graded intensity lens that is in communication with a light transmitting optical fiber and is in communication with a conical reflector. Energy is transmitted through the optical fiber, such that radiation propagating through the optical fiber projects light onto the conical reflector such that an annular light pattern, e.g., a circle, ring, halo or an outline of a shape is formed by and projected from the optical apparatus. Preferably, the light is projected through a graded intensity lens that is located between the optical fiber and the conical reflector. Use of the graded intensity lens attenuates aberrations in the light pattern and facilitates the forward annular projection of the therapeutic light. By these methods, an annular lesion can be formed in tissue. In certain embodiments, the tissue forms a lumen, e.g., vascular, atrial, brachial, uretral, etc.

The present invention further pertains to methods for forming annular lesions in cardiac tissue, e.g., trabecular tissue, by ablation, coagulation and/or phototherapeutic processes. The methods include introduction of an optical apparatus proximate to cardiac tissue via, for example, a catheter. The optical apparatus includes, for example, a graded intensity lens in communication with a light transmitting optical fiber and a conical reflector. Energy is transmitted through the optical fiber, such that radiation propagated through the optical fiber and, optionally through the GRIN lens, is reflected by the conical reflector to project forward an annular light pattern, e.g., a circle or a halo. By these methods, an annular lesion can be formed in cardiac tissue, preferably encircling the atrial tissue about the pulmonary vein, coronary sinus or other vessels.

The term "trabecular" is well recognized in the art and is intended to include tissue, e.g., cardiac tissue, which is a elastic tissue often formed of bands and cords called trabeculae consisting of fibrous tissue, elastic fibers and muscle fibers.

The present invention also pertains to methods method for treating or preventing atrial arrhythmias by ablation, coagulation or photochemical processes. The methods include introducing an optical apparatus proximate to atrial tissue via, for example, a catheter. The optical apparatus can include an optical waveguide or conical reflector in communication with a light transmitting optical fiber. Energy is transmitted through the optical fiber, such that radiation propagating through the optical fiber and waveguide or conical reflector projects an annular light pattern. The annular light pattern forms an annular lesion in the atrial tissue, thereby treating or preventing atrial fibrillation. The methods of the invention can be performed therapeutically or prophylactically.

Atrial fibrillation and atrial flutter are abnormalities in the rhythm or rate of the heart beat. For an adult at rest, the heart normally beats between 60 and 80 beats per minute, but when atrial fibrillation occurs, the atria may beat irregularly and very rapidly between 350 and 600 times per minute. This causes the ventricles to beat irregularly in response as they try to keep up with the atria. Atrial flutter is similar to atrial fibrillation. The atrial contractions are less rapid, however, usually between 200 to 400 beats per minute, and are regular. Atrial flutter is often associated with a heart attack or may occur after heart or lung surgery. Atrial fibrillation often results from a myriad of heart conditions such as angina, tachycardia, heart attack, heart valve problems, and even high blood pressure. All of these conditions can cause stretching and scarring of the atria that interfere with the heart conduction system. The heart muscle can be weakened if episodes lasting several months or longer (with rapid heart rates) occur. Briefer episodes only cause problems if the heart rate is very fast or if the patient has a serious heart problem in addition to the atrial fibrillation.

Figure 5:
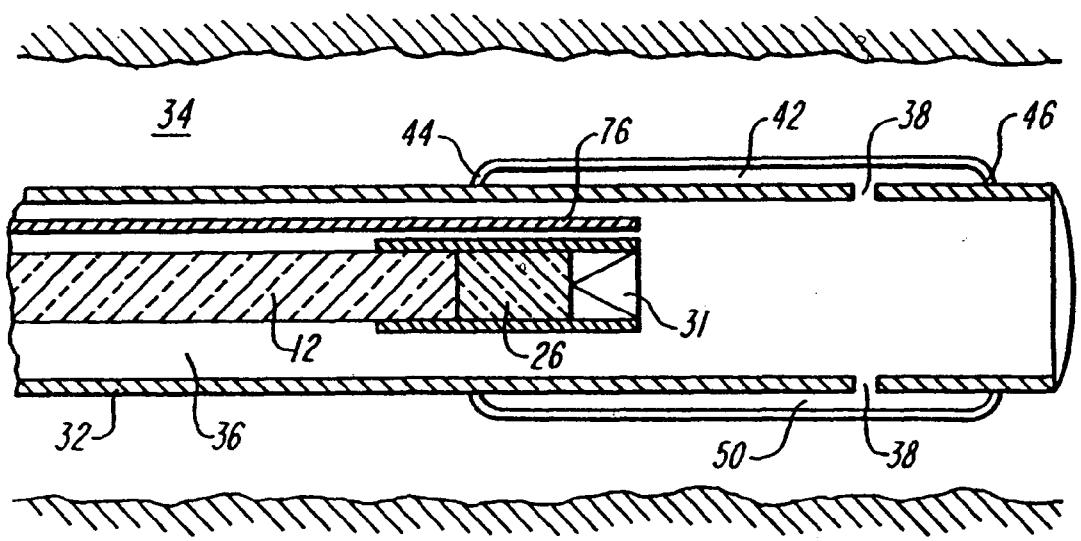
FIG. 5 is a cross-sectional view of the distal end portion of an embodiment of the invention having an optical apparatus and a balloon contained within a tubular body lumen in an uninflated state.

In FIG. 5, apparatus 30, constructed in accordance with the present invention, is depicted in its unexpanded form within a body cavity such as a lumen of a blood vessel 34. Flexible elongate member 32 includes at least one lumen 36 extending the length thereof from a proximal end to a distal end and can include, optionally, cap 48. Openings 38 in the side wall of the 32 define one or more pores that provide fluid communication between the lumen 36 and an outer balloon 42, which can be bonded at proximal end 44 and distal end 46 to flexible elongate member 32. Optical apparatus 10 can be slidably positioned within lumen 36 adjacent to balloon 42. Apparatus 30 can further include reflectance fiber 76 to monitor the progress of treatment as described infra. Optical apparatus 10 includes optical fiber 12, modified waveguide 14 and, optionally, GRIN lens 26. Alternatively, optical apparatus includes optical fiber 12, optionally, GRIN lens 26 and conical reflector 27. Injection of fluid or gas, through lumen 36 and pores 38, forces the fluid or gas to flow out of the pores 38 to fill the chamber 50 within the balloon 42, thereby inflating balloon 42. In a preferred embodiment, the balloon is spherical or teardrop shaped. Preferably, flexible elongate member 32 and balloon 42 are energy transparent.

By injecting a suitable solution or gas into chamber 50, balloon 42 can be inflated to engage body tissue (e.g., the tissue surrounding a natural or excised interstitial space within the body). In one embodiment, balloon 42 is nonporous and can engage the body tissue over a substantial portion of its length, thereby eliminating blood and/or other body fluids. A preferred inflation fluid is deuterium oxide.

Figure 7:
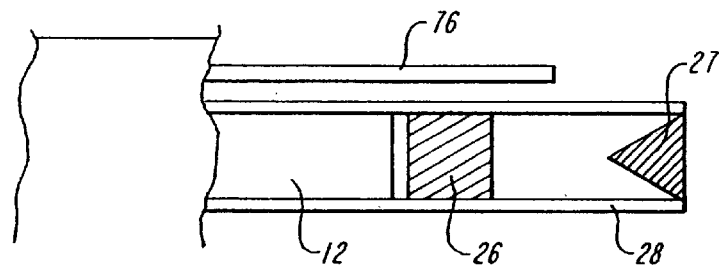
FIG. 7 is an expanded cross-sectional view of the optical apparatus of FIG. 6.

A preferred embodiment is depicted in FIGS. 6 and 7 having a silicone balloon anchor 54 (not inflated). Optical apparatus 10 can be slidably positioned within lumen 36 adjacent to balloon 42. Optical apparatus 10 includes optical fiber 12, GRIN lens 26 and conical reflector 27. Gas, e.g., air, or a liquid can be injected into lumen 36 (shown partially in phantom) to inflate silicone balloon anchor 54 if required. A solution, e.g., water, saline, or, preferably, deuterium oxide, is injected through lumen 40 to inflate balloon 42. Apparatus 30 can further include reflectance fiber 76 to monitor the progress of treatment as described infra. In one embodiment, balloon 42 is preshaped to form a parabolic like shape. This is accomplished by shaping and melting a TEFLON® film in a preshaped mold to effect the desired form. The difference in refractive index between the gas or liquid within lumen 36 and the liquid in chamber 50 facilitates the projection of annular light beam 56 to be emitted at a radical angle from light reflected from the surface of the conical reflector 27, as shown again in FIG. 7.

The devices described in FIGS. 1–7 can be used for treating, e.g., ablating, coagulating and/or phototherapeutically treating, endocardial surfaces which promote arrhythmias or other disease states or conditions. For example, atrial therapies can be performed by inserting an apparatus of the invention 30 into the femoral vein. Flexible elongate member 32 having balloon 42 fixedly attached is guided through the inferior vena cava, and into the right atrium, and if required, it is guided into the left atrium via atrial septal puncture. Left ventricular treatment can be performed by inserting flexible elongate member 32 into the femoral artery. Flexible elongate member 32 is guided through the iliac artery, the aorta, through the aortic valve and adjacent to the wall of the left ventricle. Once balloon 42 is proximate to the tissue ablation site, a solution can be injected through lumen 36 or 40 to force blood and/or body fluids away from the treatment site. Optical apparatus 10 is guided through flexible member 32 via lumen 36 to a position proximate to the tissue ablation site and energy, e.g., laser energy, is emitted through balloon 42. Preferably, the composition of flexible elongate member 32 and balloon 42 are transparent to the energy emitted through optical apparatus 10.

Figure 8:
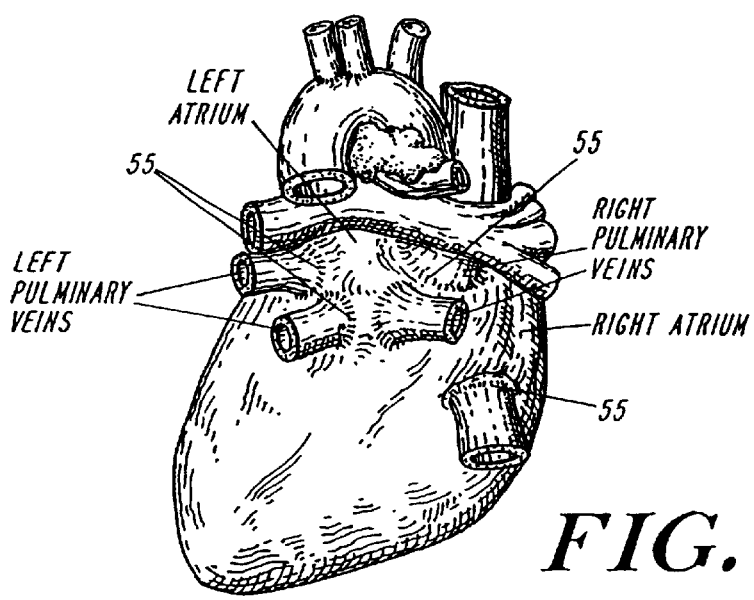
FIG. 8 is a depiction of annular lesions located at the atrium/pulmonary vein interface.

FIG. 8 depicts annular lesions 55 formed on the atrial surface encircling the pulmonary veins by the above described methods. It is considered advantageous to form the annular lesions 55 on and surrounding the atrial surface/vein interface, thereby preventing propagation of aberrant electrical waves through the cardiac region. Preferably, the lesion completely encircles the mouth of each of the target veins.

In the present invention, reflective feedback is used to monitor the state of coagulation, ablation and/or phototherapeutic processes of the treatment site so as to allow an optimal dose by either manipulation of the energy level or exposure time, or by controlling the sweep of energy across an exposure path.

Reflectance changes can also be employed by a control means in the present invention to adjust or terminate laser operation.

In another aspect of the invention, a real-time display means can be incorporated into a surgical microscope or goggles worn by a clinician during the procedure to provide a visual display of the state of tissue coagulation simultaneously with the viewing of the surgical site. The display can reveal reflectance values at one or more specific wavelengths (preferably, chosen for their sensitivity to the onset and optimal state of tissue modification), as well as display a warning of the onset of tissue carbonization.

In one method, according to the invention, application of laser to a biological structure(s) while the reflectance of light from the irradiated site is monitored. Changes in scattering due to coagulation, ablation, phototherapeutic effects or crosslinking of the tissue will cause a reflectance change. In addition, dehydration due to laser exposure also affects the site's reflection. The reflectance can be monitored in real-time to determine the optimal exposure duration or aid as visual feedback in the timing used in sweeping the energy across the treatment site during the procedure.

Figure 9:
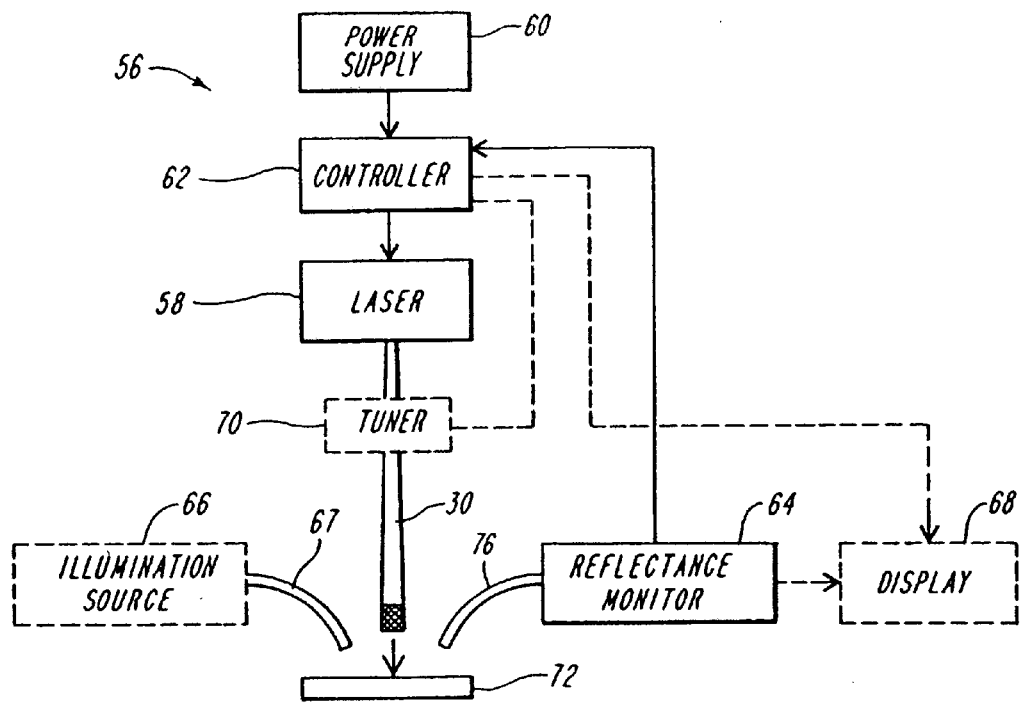
FIG. 9 is a schematic block diagram of a laser tissue treatment system according to the present invention.

In FIG. 9, a schematic block diagram of a laser tissue treatment system 57 is shown, including a laser 58, power supply 60, controller 62 and reflectance monitor 64. The system further includes optical apparatus 30, and, optionally, illumination source 66, display 68 and/or tuner 70. In use, the output of laser 58 is delivered, preferably via optical apparatus 30, to treatment site 72 to phototherapeutically treat selected tissue. As the laser beam irradiates treatment site 72 the biological tissue of the site is coagulated, ablated and/or phototherapeutically treated. The degree of treatment is determined by the reflectance monitor 64, which provides electrical signals to controller 62 in order to control the procedure. The reflectance monitor 64 receives light reflected by the site from a broadband or white light illumination source 66 via fiber 67 and/or from laser 58 via optical apparatus 30. In addition to controlling the laser operation automatically, the reflectance monitor 64 and/or controller 62 can also provide signals to a display 68 to provide visual and/or audio feedback to the clinical user. Optional tuner 70 can also be employed by the user (or automatically controlled by controller 62) to adjust the wavelength of the annealing radiation beam.

Figure 10:
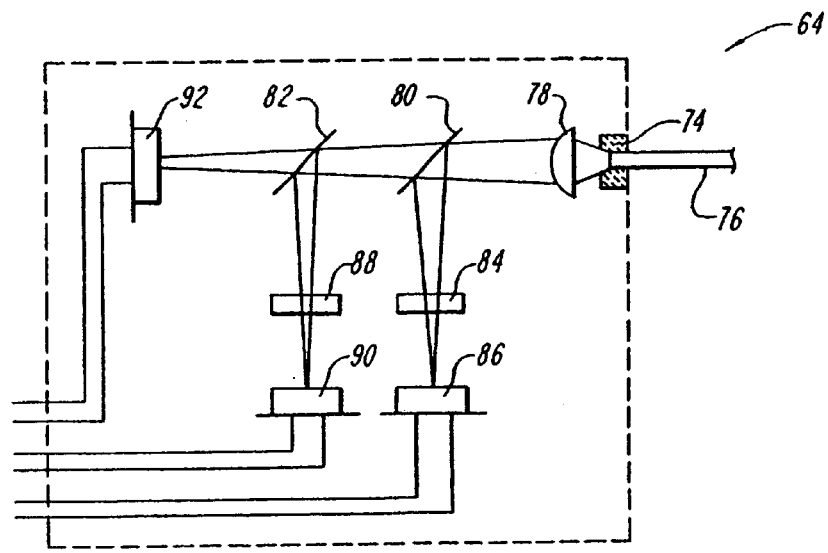
FIG. 10 is a detailed schematic diagram of a reflectance monitor for use in the present invention.

FIG. 10 is a more detailed schematic diagram of a reflectance monitor 64, including a coupling port 74 for coupling with one or more fibers 76 to receive reflectance signals. A preferred reflectance fiber is a 100 micrometer diameter silica pyrocoat fiber from Spectran (Spectran, Connecticut, part number CF04406-11). The reflectance monitor 64 can further include a focusing lens 78 and first and second beam splitting elements 80 and 82, which serve to divide the reflected light into 3 (or more) different beams for processing. As shown in FIG. 10, a first beam is transmitted to a first optical filter 84 to detector 86 (providing, for example, measurement of reflected light at wavelengths shorter than 0.7 micrometers). A second portion of the reflected light signal is transmitted by beam splitter 82 through a second optical filter 88 to detector 90 (e.g., providing measurement of light at wavelengths shorter than 1.1 micrometers). Finally, a third portion of the reflected light is transmitted to photodetector 92 (e.g., for measurement of reflected light at wavelengths greater than 1.6 micrometers). Each of the detector elements 86, 90 and 92 generate electrical signals in response to the intensity of light at particular wavelengths.

The detector elements 86, 90 and 92 can include synchronous demodulation circuitry and are used in conjunction with a modulated illumination source to suppress any artifacts caused by stray light or the ambient environment. (It should be apparent that other optical arrangements can be employed to obtain multiple wavelength analysis, including the use, for example, of dichroic elements, either as beam splitters or in conjunction with such beam splitters to effectively pass particular wavelengths to specific detector elements or spectrometers. It should also be apparent that more than three discreet wavelengths can be measured, depending upon the particular application.) The signals from the detector elements can then be transmitted to a controller and/or a display element (as shown in FIG. 9).

In the controller, signals from the reflectance monitor are analyzed to determine the degree of coagulation, ablation and/or phototherapeutic effect(s) which occurs in the biological tissue exposed to the laser radiation. Typically, such treatment is performed for 100 seconds or less. Such analysis can generate control signals that will progressively reduce the laser output energy over time as a particular site experiences cumulative exposure. The control signals can further provide for an automatic shut-off of the laser when the optimal state of treatment has been exceeded and/or the onset of carbonization is occurring.

In use, the apparatus of the present invention can be employed to analyze the degree of treatment by comparing the reflectance ratios of a site at two or more wavelengths. Preferably, intensity readings for three or more wavelength ranges are employed in order to assess accurately the degree of treatment and to ensure that the optimal state is not exceeded. The particular wavelengths to be monitored will, of course, vary with the particular tissue undergoing treatment. Although the tissue type (e.g., blood-containing tissue or that which is relatively blood-free) will vary, the general principles of the invention, as disclosed herein, can be readily applied by those skilled in the art to diverse procedures in which the phototherapeutic treatment of biological materials is desired.

Those having ordinary skill in the art will know, or be able to ascertain, using no more than routine experimentation, many equivalents to the specific embodiments of the invention described herein. These and all other equivalents are intended to be encompassed by the following claims. All publications and references cited herein including those in the background section are expressly incorporated herein by reference in their entirety.

What is claimed is:

1. A method of treating a cardiac condition comprising,
   introducing a photoablation instrument into the heart, the instrument having an optical assembly for projecting a beam of radiation;
   positioning the photoablation instrument in a location within the heart where light from the optical assembly can be projected onto an inner surface of the heart; and
   exposing a region of the heart to projected radiation the optical assembly.

2. The method of claim 1, wherein the step of exposing a region of the heart further comprises exposing a region of atrial tissue surrounding a cardiac vessel opening to an annulus of radiation from the optical assembly, thereby forming an annular lesion.

3. The method of claim 2, wherein the mean diameter of the annular lesion is greater than 10 mm.

4. The method of claim 2, wherein the mean diameter of the annular lesion is greater than 15 mm.

5. The method of claim 2, wherein the mean diameter of the annular lesion is greater than 20 mm.

6. The method of claim 2, wherein the treatment occurs in a region surrounding at least one cardiac vessel selected from the group consisting of the pulmonary vein, the coronary sinus, the inferior vena cava and the superior vena cava.

7. The method of claim 2, wherein the annular lesion has a width of less than 5 mm.

8. The method of claim 2, wherein the annular lesion has a width of less than 3 mm.

9. The method of claim 2, wherein the annular lesion has a width of less than 1 mm.

10. A method of treating atrial arrhythmia comprising:
introducing a photoablation instrument into an atrium, the instrument having an optical assembly for projecting an annular beam of radiation;
positioning the photoablation instrument in a location within the atrium where light from the optical assembly can be projected onto an inner surface of the atrium; and
exposing a region of atrial tissue to an annulus of projected radiation from the optical assembly, thereby forming an annular lesion.

11. The method of claim 10, wherein the projected light surrounds a pulmonary vein thereby forming an annular lesion within the heart around the pulmonary vein.

12. The method of claim 10, wherein the projected light surrounds the coronary sinus thereby forming an annular lesion within the heart around the coronary sinus.

13. A method of treating atrial arrhythmia comprising:
introducing a photoablation instrument into an atrium, the instrument having an optical assembly for projecting a beam of radiation;
positioning the photoablation instrument in a location within the atrium where light from the optical assembly can be projected onto an inner surface of the atrium; and
exposing a region of atrial tissue surrounding a pulmonary vein to projected radiation from the optical assembly at a wavelength ranging from about 805 nm to about 1060 nm.

14. The method of claim 13, wherein the wavelength ranges from about 900 nm to about 1000 nm.

15. The method of claim 13, wherein the wavelength ranges from about 940 nm to about 980 mm.

16. The method of claim 13, wherein the energy and wavelength of the radiation are chosen to penetrate substantially the entire thickness of the atrial wall.

17. A method of treating atrial arrhythmia comprising:
introducing a photoablation instrument into an atrium, the instrument having an optical assembly and an expandable balloon element adapted to surround the optical assembly upon inflation;
inflating the balloon element with an inflation fluid, such that the inflated balloon provides a transmission pathway for radiation between the optical assembly and an inner surface of the atrium; and
exposing a region of atrial tissue surrounding a pulmonary vein projected radiation from the optical assembly.

18. The method of claim 17, wherein the inflation fluid is deuterium oxide.

19. The method of claim 17, wherein the radiation has a wavelength range from about 900 nm to about 1000 nm.

20. The method of claim 17, wherein the radiation has a wavelength ranges from about 940 nm to about 980 nm.

21. The method of claim 17, wherein the energy and wavelength of the radiation are chosen to penetrate substantially the entire thickness of the atrial wall.

22. The method of claim 17, wherein the radiation is projected as an annular beam, thereby forming an annular lesion.

23. The method of claim 22, wherein the mean diameter of the annular lesion is greater than 10 mm.

24. The method of claim 22, wherein the mean diameter of the annular lesion is greater than 15 mm.

25. The method of claim 22, wherein the mean diameter of the annular lesion is greater than 20 mm.

26. The method of claim 22, wherein the treatment occurs without substantial ablation of pulmonary vein tissue.

27. The method of claim 22, wherein the annular lesion has a width of less than 5 mm.

28. The method of claim 22, wherein the annular lesion has a width of less than 3 mm.

29. The method of claim 22, wherein the annular lesion has a width of less than 1 mm.

* * * * *

UNITED STATES PATENT AND TRADEMARK OFFICE
CERTIFICATE OF CORRECTION

PATENT NO.    : 6,572,609 B1                                            Page 1 of 1
DATED         : June 3, 2003
INVENTOR(S)   : Norman E. Farr et al.

It is certified that error appears in the above-identified patent and that said Letters Patent is hereby corrected as shown below:

Column 20,
Line 50, replace "radiation the" with -- radiation from the --; and

Column 22,
Line 14, replace "vein projected" with -- vein to projected --.

Signed and Sealed this

Twenty-second Day of July, 2003

JAMES E. ROGAN
*Director of the United States Patent and Trademark Office*